(12) United States Patent
Rovatti et al.

(10) Patent No.: US 10,485,912 B2
(45) Date of Patent: Nov. 26, 2019

(54) EXTRACORPOREAL BLOOD TREATMENT SYSTEM FOR INDIVIDUALIZED TREATMENT

(71) Applicant: GAMBRO LUNDIA AB, Lund (SE)

(72) Inventors: Paolo Rovatti, Finale Emilia (IT); Alessandro Surace, Carpi (IT)

(73) Assignee: Gambro Lundia AB, Lund (SE)

( * ) Notice: Subject to any disclaimer, the term of this patent is extended or adjusted under 35 U.S.C. 154(b) by 336 days.

(21) Appl. No.: 15/103,174

(22) PCT Filed: Dec. 10, 2014

(86) PCT No.: PCT/EP2014/077104
§ 371 (c)(1),
(2) Date: Jun. 9, 2016

(87) PCT Pub. No.: WO2015/086631
PCT Pub. Date: Jun. 18, 2015

(65) Prior Publication Data
US 2016/0303303 A1    Oct. 20, 2016

(30) Foreign Application Priority Data
Dec. 10, 2013 (EP) .................................. 13196451

(51) Int. Cl.
*A61M 1/16* (2006.01)

(52) U.S. Cl.
CPC ........ *A61M 1/1611* (2014.02); *A61M 1/1601* (2014.02); *A61M 1/1652* (2014.02);
(Continued)

(58) Field of Classification Search
CPC ................................................ A61M 2205/52
See application file for complete search history.

(56) References Cited

U.S. PATENT DOCUMENTS

| 2005/0102165 A1* | 5/2005 | Oshita ................ A61M 1/14 705/3 |
| 2011/0077574 A1 | 3/2011 | Sigg et al. |

(Continued)

FOREIGN PATENT DOCUMENTS

| EP | 2597584 | 5/2013 |
| WO | 93/01845 | 2/1993 |

(Continued)

OTHER PUBLICATIONS

International Search Report PCT/EP2014/077104—dated Mar. 11, 2015—5 pages.

(Continued)

*Primary Examiner* — Bobby Ramdhanie
*Assistant Examiner* — Michael J An
(74) *Attorney, Agent, or Firm* — K&L Gates LLP

(57) ABSTRACT

A method of operating an extracorporeal blood treatment includes, prior to commencing an extracorporeal blood treatment, reading from a storage device (4a, 5a) stored values of a patient-specific prescription parameter. These stored values relate to a sequence of previous extracorporeal blood treatments. In addition, the method includes processing the stored values of the parameter read from the storage device (4a, 5a) according to a predetermined algorithm to determine a current value of the patient-specific prescription parameter. The current value is then available for the subsequent extracorporeal blood treatment.

34 Claims, 2 Drawing Sheets

(52) U.S. Cl.
CPC ... *A61M 1/1613* (2014.02); *A61M 2205/3576* (2013.01); *A61M 2205/3584* (2013.01); *A61M 2205/52* (2013.01); *A61M 2205/6018* (2013.01); *A61M 2205/6054* (2013.01)

(56) References Cited

U.S. PATENT DOCUMENTS

| 2011/0118647 A1* | 5/2011 | Paolini | A61M 1/16 |
| | | | 604/6.09 |
| 2013/0274642 A1* | 10/2013 | Soykan | A61M 1/28 |
| | | | 604/5.01 |

FOREIGN PATENT DOCUMENTS

| WO | 2010/108955 | 9/2010 |
| WO | 2012/038384 | 3/2012 |

OTHER PUBLICATIONS

Written Opinion of the International Searching Authority—dated Mar. 11, 2015—6 pages.

* cited by examiner

EXTRACORPOREAL BLOOD TREATMENT SYSTEM FOR INDIVIDUALIZED TREATMENT

PRIORITY CLAIM

The present application is a National Phase of International Application No. PCT/EP2014/077104, filed on Dec. 10, 2014, which claims priority to European Patent Application No. 13196451.2, filed Dec. 10, 2013, the entire contents of each of which are incorporated herein by reference and relied upon.

The technology described herein relates generally to treating blood outside (i.e., extracorporeal) of a patient's body. More specifically, the technology relates to an extracorporeal blood treatment system and a method of operating such a blood treatment system that enable improved individualized treatment.

An extracorporeal blood treatment involves removing blood from a patient, treating the blood outside the patient's body, and returning the treated blood to the patient. Extracorporeal blood treatment may be used to extract undesirable substances or molecules from the patient's blood, and, if necessary, to add desirable substances or molecules to the blood. An extracorporeal treatment of blood may be required, for example, when a patient's kidneys are unable—whether temporarily or permanently—to effectively remove substances from the blood. The patient is then required to undergo extracorporeal blood treatment to add or remove substances to the blood, to maintain a certain acid/base balance or to remove excess body fluids, for example.

This is typically accomplished by passing blood through a treatment unit, e.g., a dialyzer or a hemofilter. Blood is removed from the patient in, e.g., a continuous flow, and introduced into a primary chamber, also referred to as blood chamber, of the treatment unit. Therein, the blood flows past a semipermeable membrane that selectively allows matter in the blood to cross the membrane from the primary chamber into a secondary chamber and also selectively allows matter in the secondary chamber to cross the membrane into the blood in the primary chamber, depending on the type of treatment. The secondary chamber is also referred to as fluid chamber.

A number of different types of extracorporeal blood treatments may be performed. In an ultrafiltration (UF) treatment, undesirable matter is removed from the blood by convection across a membrane into the secondary chamber. In a hemofiltration (HF) treatment, the blood flows past the semipermeable membrane as in UF and desirable matter is added to the blood, typically by dispensing a fluid into the blood either before and/or after it passes through the treatment unit and before it is returned to the patient. In a hemodialysis (HD) treatment, a secondary fluid containing desirable matter is introduced into the secondary chamber of the treatment unit. Undesirable matter from the blood crosses the semipermeable membrane into the secondary fluid and desirable matter from the secondary fluid may cross the membrane into the blood. In a hemodiafiltration (HDF) treatment, blood and secondary fluid exchange matter as in HD, and, in addition, matter is added to the blood, typically by dispensing a fluid into the treated blood before its return to the patient as in HF.

EP 2293829 discloses an exemplary extracorporeal blood treatment apparatus having a dialyzer and a blood circuit that interconnects the dialyzer and the patient. By means of that apparatus, the well-being of the patient during a dialysis treatment is improved as it allows individualizing the treatment. That is, a weight loss system of the apparatus is controlled on the basis of patient-specific prescription parameters, in that case, the patient's hematic volume change and the patient's desired weight loss. During machine setting, input of a total weight loss value is also required, and a percentage variation of the blood volume to be obtained at the end of treatment is calculated on the basis of the percentage weight loss and the preset value of the refilling index. Starting from this desired value of percentage variation of the blood volume at the end of the treatment, a desired profile of the variation is calculated starting from an initial value.

An article entitled "A new method to evaluate patient characteristic response to ultrafiltration during hemodialysis", published in "The International Journal of Artificial Organs", Vol. 30, no. 5, 2007, discloses that a plasma refilling index (PRI) parameter, defined by the relation between the total body water of an individual and the blood volume, provides a useful indication for evaluating the response of a patient subject to dialysis, in particular his or her behavior in relation to vascular "refilling", i.e., the quantity of liquid which is displaced from the interstitial space of the patient's body to the intravascular space.

If, e.g., kidney dialysis takes place in a dialysis center or a hospital, a nurse or patient care technician usually interacts with a patient subject to dialysis treatment. To ensure the safety of the patient and the quality of treatment, well defined instructions and procedures prescribe the various actions a nurse has to perform before, during and at the end of a treatment session. For example, the instructions require the nurse to read numerous parameters and settings from a user interface, to use them for additional calculations, and to note the parameters, settings, and any calculation results in a treatment record, such as total UF amount removed, last available estimated clearance, current cumulative Kt/V, % recirculation, water/plasma refilling index, and final blood volume % (BV %). Some of these recorded parameters are then used as prescription parameters or as a base for calculating other prescription parameters for the next treatments of the patient.

Although known external blood treatment apparatuses, such as dialysis machines, provide for automatic control of a treatment, calculations and manual recordings of patient-specific parameters may still be required by a nurse at the end of a treatment, in particular if a more individualized treatment is desired. This is time consuming and prone to errors, which may negatively affect the quality of treatment. Further, the requirement for calculating and recording these patient-specific parameters at the end of each treatment may be perceived as an obstacle to further the use or introduction of individualized treatments.

There is, therefore, a need for an improved technology for extracorporeal treatment of blood, in particular with respect to the operability of the apparatus and patient safety. The improved technology provides for further automatic operation of an extracorporeal blood treatment system that is able to effectively adapt to the various characteristics and needs of each patient in order to individualize treatment and to guarantee patient well-being during treatment. Further, the improved technology ensures that the patient receives an optimized treatment therapy through the adaptation of some prescription parameters by means of tracking his/her body condition.

Accordingly, one aspect involves an extracorporeal blood treatment system having a first holder, a second holder and a control unit. When the system is in use, the first holder holds a blood treatment device having a blood chamber, a fluid chamber and a semipermeable membrane that separates the chambers from each other. When the system is in use, the second holder holds an extracorporeal blood circuit coupled to the blood treatment device. The control unit is configured to operate at least one pump to cause blood to flow through the blood treatment device and the extracorporeal blood circuit. The control unit is further configured to execute a procedure that reads prior to commencing an extracorporeal blood treatment from a storage device stored values of a patient-specific prescription parameter. The stored values relate to previous extracorporeal blood treatments. The procedure further processes the stored values of the prescription parameter read from the storage device according to a predetermined alogrithm to determine a current value of the patient-specific prescription parameter. The current value is then available for the subsequent extracorporeal blood treatment.

Accordingly, the algorithm provides a result that is available for futher use. The result should fall within a predetermined range of acceptability, i.e., a range that is reasonable from a physiological point of view. For example, a water refilling index should typically be between about 0.5 and about 2.0. If that is the case, the result is deemed "valid," if not, the result is discarded (e.g., not stored). Once the result is valid, the system is in one embodiment configured to use the result as a set value for the patient-specific prescription parameter, or to suggest it to the user and requiring him/her to either accept or to discard the suggested parameter. For example, the new value can be displayed as a suggested value on a monitor of the system, and the user may accept the suggested new value for the subsequent treatment by pressing a dedicated button or area, e.g., on a touch screen.

The procedure can be performed the first time a certain patient-specific prescription parameter has to be used, but is not yet available as prescription parameter. In another embodiment, the procedure can be performed every time the user decides to rerun a patient characterization for that patient-specific presciprion parameter, e.g., when in doubt whether or not the patient's physical characteristics have changed, or after a specific time interval (e.g., defined to be a routine procedure in the clinic).

In one embodiment, the procedure can be continuously applied in order to precisely track any drift of the patient's physical characteristics. In such an embodiment, a continuous patient identification and trending functionality can be implemented in the system.

As described above, there may be doubt or drift regarding the patient's physical characteristics. In such cases, at each treatment, the new value of the patient-specific prescription parameter calculated by the algorithm is used or suggested (on the basis of the previously described configuration option) only if the new value exceeds a predefined threshold. This threshold may be defined as a physiologically significant percentage. That is, if the new value deviates by more than this percentage from the previously used patient-specific prescription parameter, the patient's physical characteristic has significantly changed and the new value is used or suggested.

Another aspect involves a method of operating such an extracorporeal blood treatment. Prior to commencing an extracorporeal blood treatment, the method reads from a storage device stored values of a patient-specific prescription parameter. These stored values relate to a sequence of previous extracorporeal blood treatments. In addition, the method processes the stored values of the parameter read from the storage device according to a predetermined algorithm to determine a current value of the patient-specific prescription parameter. The current value is then available for the subsequent extracorporeal blood treatment.

In one embodiment, a value of the patient-specific prescription parameter is stored in the storage device at the end of each treatment. Depending on how the storage device is configured, the storing occurs automatically, e.g., when the storage device is internal (e.g., an internal non volative memory of the machine), or by asking the operator to make the storage device available for being written by the machine, e.g., coupling the storage device to the system when the storage device is external (e.g., a memory card). Advantageously, the user/nurse is no longer required to manually collect, record and/or process data at the end of each treatment.

In one embodiment, it is determined that a run-in period is complete when a predetermined number of values has been stored. This allows obtaining an initial value of a selected patient-specific prescription parameter. A subsequent treatment according to a desired therapy can then use that initial value as a starting point.

In one embodiment, the stored values are read according to a predetermined pattern. The pattern may be defined to read N consecutive stored values, wherein N may represent the number treatments performed during the run-in period.

In one embodiment, the predetermined algorithm determines an average value (e.g., arithmetic mean, or median) of the stored values read from the storage device. Advantageously, using the average value provides for a better reference for the actual medical condition of the patient, leveling out any "bad day" the patient may have. It is contemplated that the predetermined algorithm may apply any other statistical parameter (e.g., standard deviation) that allows assessing the patient's medical condition over a certain period of time.

In one embodiment, a default value is used as the current value if less than a threshold number of stored values is read. The default value may be set by a physician responsible for the patient's treatment. This provides for flexibility if the desired therapy needs to be started before the run-in period is complete.

Advantageously, the storage device used in connection with the technology described herein may have a variety of different configurations, and be internal or external to the system. It may be configured as a portable patient card that is used at the treatment site (e.g., configured as a chip card, magnetic card, RFID card, USB memory device or disc storage device). Alternatively, it may be located within a computer system at the treatment site (i.e., local) or at a remote site. In a computer system, the storage device may be any kind of known storage medium, e.g., a disc drive.

As to the structure of the system, the technology allows substantial flexibility. In one embodiment, the system includes a network interface for communications with a (remote or local) computer system that includes a storage device. In another embodiment, the system includes a communications interface for communications with a storage device. Depending on a specific configuration, one or all of these interfaces may be implemented on the apparatus.

It is a further advantage of the technology described herein that a variety of patient-specific prescription parameters can be selected. Examples of such patient-specific prescription parameters include the water-refilling index WRI, (final) relative blood volume ($\Delta$BV), (final) blood volume (BV %), and variation of weight loss ($\Delta$WL %). It is contemplated that any other prescription parameter that can be determined by a collection of the patient related parameters at the end of a treatment can be used. Additional exemplary parameters are prescribed total ultrafiltration (total UF prescribed), distribution volume, sodium mass transfer, kT/V (parameter for dialysis dose, used to quantify dialysis treatment adequacy, wherein K is the dialyzer clearance of urea, t the dialysis time and V the volume of distribution of urea), total subsitution volume, drop of arterial and venous pressures (initial versus end of treatment session), and drop of plasma conductivity (initial versus end of treatment session).

In addition to the foregoing, the improved technology allows monitoring of a patient's therapy over time and determining a trend, if any, (also referred to as "trending") of a patient-specific prescription parameter. That trending is performed by the extracorporeal blood treatment system, or by the apparatus alone. In one embodiment, the trending is performed automatically and continuously with a minimum of user/nurse interaction. That further ensures that a patient receives the correct prescription in a safer way.

The technology described herein stores values of a patient-specific prescription parameter in a storage device that may have a number of configurations, as mentioned above. An advantage of using the storage device is that all data relevant for performing the trending is stored in the same location and in the same format which facilitates data handling and processing.

It is contemplated that the extracorporeal blood treatment system is operated in accordance with the technology described herein prior to commencing an extracorporeal blood treatment. The technology as such is, therefore, not applied while a patient is undergoing extracorporeal blood treatment.

The novel features and method steps characteristic of the invention are set out in the claims below. The invention itself, however, as well as other features and advantages thereof, are best understood by reference to the detailed description, which follows, when read in conjunction with the accompanying drawings, wherein:

Figure 1:
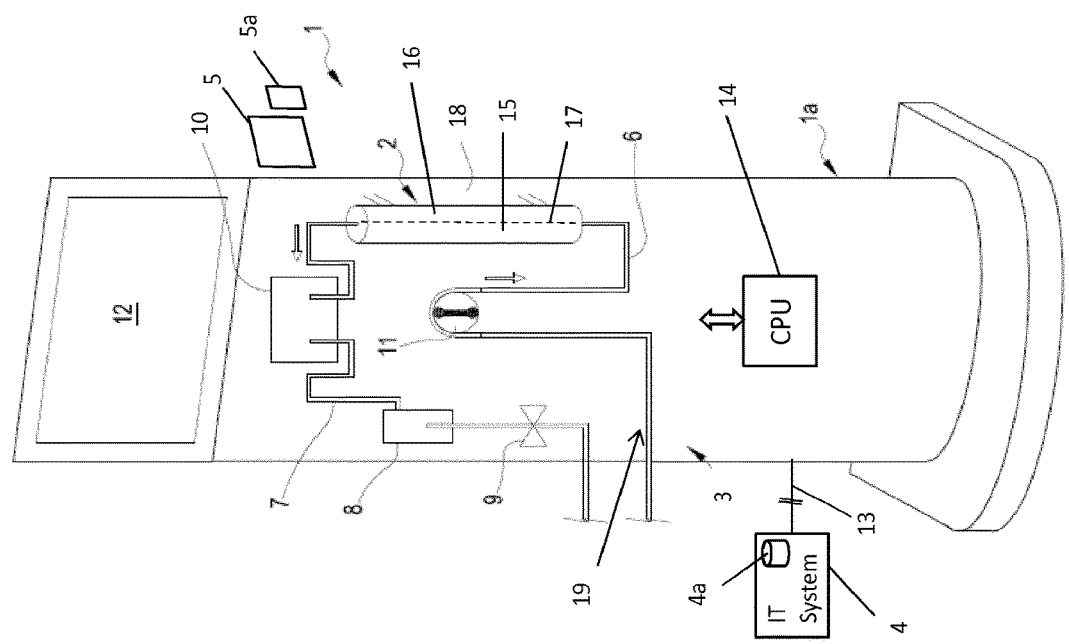
FIG. 1 shows a schematic illustration of one embodiment of an extracorporeal blood treatment system.

FIG. 1 is a schematic illustration of one embodiment of an extracorporeal blood treatment system in which the technology described herein is implemented. The illustrated system has an extracorporeal blood treatment apparatus 1 (also "apparatus 1") having a housing 1a that houses a user interface 12, a pump 11 and a control unit 14 (labeled as CPU in FIG. 1). Further, the housing 1a holds a treatment unit 2, and components of an extracorporeal blood circuit 3. The user interface 12 may include a display screen and a keypad, a touch screen or a combination thereof. For the sake of completeness, additional details regarding various optional embodiments of the extracorporeal blood circuit 3 and associated components, such as sensors and actuators, are described below.

In the embodiment of FIG. 1, the system includes further a computer system 4 (labeled as IT System in FIG. 1) having an internal or external storage device 4a and being coupled to the apparatus 1 via a network 13 and a network interface (not shown). The apparatus 1 includes a communications interface 5 for communicating with a storage device 5a. It is contemplated that the computer system 4, the network 13 and the communications interface 5 may be optional and may therefore not be present in all embodiments. Further, depending on a particular embodiment, the system 1 may have only one of the communications interface 5 and the computer system 4 including the network 13, or all of these components.

The computer system 4 may be located away from the apparatus 1, e.g., in another room of the same building as the apparatus 1 (which may still be considered to be "local"), wherein the network 13 is a local area network (LAN) based on any technology that enables (bi-directional) communications between computerized entities (here, the computer system 4 and the apparatus 1). Examples of such technologies include wire-based technologies (e.g., an Ethernet LAN) or wireless technologies (e.g., a (WiFi) WLAN), or a combination of these technologies.

The computer system 4 may be located even further away from the apparatus 1, e.g., in a different city. Communications between these remotely located entities (here, the computer system 4 and the apparatus 1) occur then via a wide area network (WAN) and/or the internet, applying again wire-based or wireless technologies, or any other communications technology.

It is contemplated that more than one apparatus 1 may be coupled to the computer system 4. For example, in a dialysis center, a physician/nephrologist may be centrally located at or near the computer system 4 and monitor treatments taking place at several apparatuses 1 at patients' sites. For that reason, the computer system 4 has a user interface (not shown) with input and output functionalities, and the storage device 4a to keep electronic patient records and to store patient-specific data.

The communications interface 5 is configured to communicate with at least one of several types of storage device. For example, the storage device 5a may be a proximity card based on known near field communication (NFC)/RFID technology, and the communications interface 5 may be a so-called RFID card reader. The card reader can activate the proximity card via an antenna embedded in the card and read/write data from/to a memory also embedded in the card. Alternatively, the storage device 5a may be a magnetic card, a flash-memory (e.g., in form of a USB memory stick), a disc drive or any other kind of storage device or storage medium with read/write functionality. It is contemplated that the communications interface 5 is configured to be compatible with the selected kind of storage device 5a. That is, for example, both the communications interface 5 and the storage device 5a implement RFID technology or USB technology.

Regardless of a specific physical configuration, the storage device 5a may be referred to as "patient card" that carries patient-specific data (e.g., personal data (e.g., name, age) and treatment data (e.g., prescription, treatment parameters). The patient card is removable/detachable from the apparatus 1, or needs to be brought within an operative range only during a read or write operation. Advantageously, such a patient card is easy to handle and portable (i.e., not fixedly installed in the apparatus 1) so that the patient data is not stored within the apparatus 1. Patient data is thereby conveniently transferable, which, for example, avoids having to treat the patient always on the same apparatus 1. This means also that the improved technology described herein not only uses the patient card in a conventional way (i.e., to store patient data like name, age etc.), but also for a new purpose, i.e., as a storage media for the values of the patient-specific prescription parameter, as described herein.

The control unit 14 is configured or programmed to operate the apparatus 1 during all stages of a treatment. For that purpose, the control unit 14 has a (central) processing unit (CPU) coupled to or containing a data storage for storing computer-readable instructions/programs or data. It is contemplated, that—as an alternative to an embodiment using a patient card or the storage device 4a—the data storage may in one embodiment store patient-specific data so that that kind of data is stored within the apparatus 1. The data storage may comprise a mass storage device based on one of a variety of technologies, for example, optical or magnetic, a re-programmable memory (EPROM, FLASH) or other known storage media. In addition, the control unit 14 is coupled to the user interface 12 and other components of the apparatus 1 by means of a communications bus or control lines, or a combination thereof.

For example, during the set-up stage, the control unit 14 communicates with the user interface 12 to enable entry of patient-specific data (personal and prescription data (e.g., kind of therapy (HD, HDF, HF), dialysis target values, dialysis duration). In one embodiment, the control unit 14 activates the communications device 5 to read data from a patient card. During the treatment stage, i.e., when the patient is connected to the apparatus 1 and blood flows through the extracorporeal blood circuit 3, the control unit 14 controls operation of the pump 11, sensors and actuators according to the prescribed therapy (e.g., HD, HDF, HF), processes control parameters (e.g., sensor readings, actuator settings), and displays one or more of the processing results, sensor readings and actuator settings on a screen of the user interface 12. At the end of the treatment, the control unit 14 obtains the final values of several patient-specific prescription parameters, which may be displayed on the screen.

As such, the patient-specific prescription parameter is an end-of-treatment parameter. Examples of such patient-specific prescription parameters include the water-refilling index WRI, (final) relative blood volume (ΔBV), (final) blood volume (BV %), and variation of weight loss (ΔWL %). It is contemplated that any other prescription parameter that can be determined by a collection of the patient related parameters at the end of a treatment can be used. Additional exemplary parameters are prescribed total ultrafiltration (total UF prescribed), distribution volume, sodium mass transfer, kT/V (parameter for dialysis dose, used to quantify dialysis treatment adequacy, wherein K is the dialyzer clearance of urea, t the dialysis time and V the volume of distribution of urea), total subsitution volume, drop of arterial and venous pressures (initial versus end of treatment session), and drop of plasma conductivity (invitial versus end of treatment session).

In one embodiment of the prior art, the nurse is at that end-of-treatment state required to manually record these final values. Depending on a hospital's or center's procedures, the nurse may further be required to process the values to obtain, e.g., parameters such as the ratio final blood volume % to total UF, or other parameters.

Figure 2:
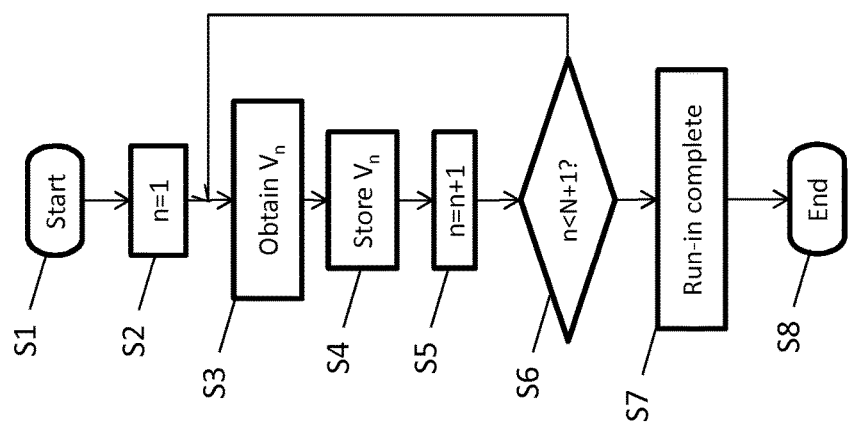
FIG. 2 is a flowchart of one embodiment of a method of operating the extracorporeal blood treatment system of FIG. 1 to read stored data.

To improve upon the prior art, the control unit 14 is configured and programmed to perform the procedures described hereinafter with reference to FIG. 2 and FIG. 3. FIG. 2 is a flowchart of one embodiment of a method of operating the extracorporeal blood treatment system of FIG. 1. That method takes place during a so-called run-in period and serves to obtain initial data for use in subsequent treatments.

A run-in period may be defined as a predetermined number of treatments, e.g., six consecutive treatments. The run-in period is for determining a certain number of values of patient-specific prescription parameters at the end of each treatment, and for learning about the patient's physical characteristics or response to these treatments. The run-in period may be selected, for example, when the patient starts with external blood treatment for the first time, or when the patient changes to a different kind of external blood therapy. It is contemplated that the patient already undergoes effective external blood treatment during the run-in period, even though it may be a relatively standardized treatment instead of a more individualized treatment that uses past/historic data of the patient.

The method starts at a step S1 at the end of a treatment, and ends at a step S8. Intermediate steps S3 and S4 define certain tasks that are repeated a certain number of times, here N times, wherein N is set according to the length of the run-in period. In one embodiment, the run-in period may be defined as six consecutive treatments, i.e., N=6.

In a step S2, the method sets a counter variable n initially to 1, and in a step S3, the method obtains a value $V_n$ of a patient-specific prescription parameter. With n=1, the first obtained value is $V_1$.

Referring to the step S4, the method stores the value $V_n$.

Depending on a specific embodiment, the value $V_n$ is stored in one of the storage devices 4a, 5a, or both, together with the time and the date of storing. Storing the value $V_n$ assumes that it is "valid", i.e., falls within a predetermined range that is reasonable from a physiological point of view. For example, a water refilling index (WRI) should typically be between about 0.5 and about 2.0. If that is the case, the result is deemed "valid," if not, the result is discarded (e.g., not stored). Advantageously, this protects against storing "wrong" values and ensures that only valid values are stored.

In a step S5, the counter value n is incremented by 1, and in a step S6, the method determines if the steps S3 and S4 have been repeated N times. If so (i.e., n is not <N+1), the method proceeds along the NO branch to a step S7. At the end of that loop and with N=6, the obtained values are $V_1 \ldots V_N$.

In the step S7, the method determines that the run-in period is complete. That determination may be displayed on the user interface 12. After that, the method ends at step S8.

The run-in period described with reference to FIG. 2, provides the initial value of the patient-specific prescription parameter for the following treatment. One example of a specific dialysis treatment is a HemoControl™ treatment mode implemented in an ARTIS™ monitor available from Gambro Lundia, AB. Such a treatment adapts therapies to individual patients. With automated profiling of UF rate and $Na^+$ level, therapies in that treatment mode manage fluid. The UF rate and $Na^+$ level are automatically adjusted to reach the treatment goals while keeping blood volume stable and within a trajectory where hypovolemia tends to be avoided.

At the end of the run-in period, a buffer implemented in one or both of the storage devices 4a, 5a, or in an internal storage device contains the predetermined number of values of the patient-specific prescription parameter. With the improved technology described herein, however, storing values after each treatment does not stop at the end of the run-in period. Instead, the apparatus 1 is configured to continue with storing, i.e., to automatically store values of the selected patient-specific prescription parameter after each treatment that follows the run-in period. The buffer, therefore, contains in one embodiment always the "valid" values of the last N treatments. The buffer may be configured as a first in, first out (FIFO) buffer.

It is contemplated that the storage devices 4a, 5a may apply any known technology for storing, organizing and/or manipulating data on a storage device as long the data is readable according to a selected pattern. For example, the storage device 4a, 5a may be organized in tables with variables and cells that are addressable by a pointer.

Figure 3:
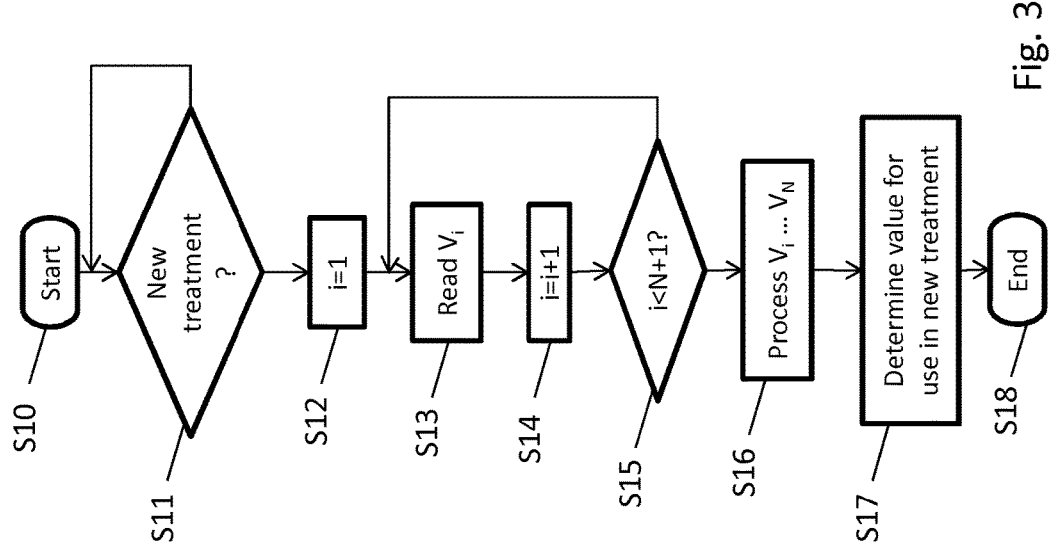
FIG. 3 is a flowchart of one embodiment of a method of operating the extracorporeal blood treatment system of FIG. 1 to store data.

FIG. 3 is a flowchart of another embodiment of a method of operating the extracorporeal blood treatment system of FIG. 1. In one exemplary scenario, that method takes place after the run-in and before a new treatment.

The method starts at a step S10, and ends at a step S18. In a step S11, the method determines if the apparatus 1 is about to begin a new treatment. If so, the method proceeds along the YES branch to a step S12. In the step S12, a counter variable i is initially set to 1.

Referring to a step S13, the method reads a value $V_i$ of a patient-specific prescription parameter from one of the storage devices 4a, 5a. Similar to the loop in the method of FIG. 2, the method repeats the step S13 N times (see steps S14, S15) so that N (e.g., N=6) values of the patient-specific prescription parameter are available when the method proceeds along the NO branch to a step S16.

In the step S16, the method processes the values $V_i$ to $V_N$. That processing is carried out according to a predetermined algorithm. For example, the algorithm calculates in one embodiment the average of the values $V_i$ to $V_N$, e.g., the arithmetic mean. With N=6, the arithmetic mean is $(V_1 + \ldots + V_6)/6$.

In a step S17, the method determines that the value of the patient-specific prescription parameter calculated in the step S16 is the value to be used in the treatment that is about to begin. Unlike a standard value, that value of the patient-specific prescription parameter is individual for the patient and contributes to individualize the treatment. The method ends in the step S18.

As mentioned above, the method illustrated in FIG. 3 assumes that the run-in period has been completed so that at least N values are available (stored) for processing. However, under certain circumstances (e.g., a nurse forgot to store the data onto the card so that the number of valid values is less than six), the run-in period may not yet be complete and less than N values may be stored. In that situation, the apparatus 1 suggests a default value, e.g., WRI=1 defined by the physician responsible for the patient's treatment, and generates a message notifying the user that the default value is suggested because the run-in period was not complete.

Alternatively, in such a situation, the apparatus 1 may use any available stored value and calculate a mean value of these values. If that mean value deviates too much from the stored default value (e.g., by more than 10%), the default value is used.

When the apparatus 1 is set to perform the desired therapy (e.g., HemoControl™), it is contemplated that the apparatus 1 executes the method illustrated in FIG. 3 at the beginning of each treatment. In one exemplary embodiment, the apparatus 1 reads according to a selected pattern, e.g., the last six values of the water refilling index (WRI) from the patient card (e.g., storage device 5a) at the beginning of a treatment. If the buffer on the patient card is full, the apparatus 1 automatically calculates the average WRI of the last six treatments and suggests this average WRI for the current treatment. Should the buffer not be full, the apparatus 1 suggests a default value, e.g., WRI=1, and notifies the user accordingly.

As this procedure is executed before each treatment with values from the last N treatments, an "observation window" is implemented that moves over time (e.g., a window of six treatments extends over the last two weeks). This provides for a continuous monitoring of the patient-specific prescription parameter and allows recognizing if any changes of the patient-specific prescription parameter show any trend. Further, the apparatus 1 may generate a message/alarm if the patient-specific prescription parameter deviates from the trend by more than a set threshold. In this case, the apparatus 1 suggests in one embodiment the average of the patient-specific prescription parameter of the last six treatments to the user.

Returning to the structure of the system 1, the treatment unit 2 has a primary chamber 15 and a secondary chamber 16 separated by a semipermeable membrane 17. Depending on the therapy, the membrane 17 may be selected to have different properties and performances. For example, the treatment unit 2 may be configured as a hemofilter, a hemodiafilter, a plasma filter, or a dialysis filter. A blood withdrawal line 6 of the extracorporeal blood circuit 3 is connected to an inlet of the primary chamber 15, and a blood return line 7 of the extracorporeal blood circuit 3 is connected to an outlet of the primary chamber 15. The treatment unit 2 is replaceably mounted by a holder 18 to a front panel or a side panel of the housing 1a of the apparatus 1. Similarly, the extracorporeal blood circuit 3 is replaceably mounted by a holder 19 to a front panel or a side panel of the housing 1a.

In use, the blood withdrawal line 6 and the blood return line 7 are connected to a needle or to a catheter or other access device (not shown) which is then placed in fluid communication with the patient's vascular system, such that blood can be withdrawn through the blood withdrawal line 6, passed through the primary chamber 15 and then returned to the patient's vascular system through the blood return line 7.

An air separator, such as a bubble trap 8, may be inserted into the blood return line 7. Moreover, a safety clamp 9 controlled by the control unit 14 may be present on the blood return line 7 downstream the bubble trap 8. A bubble sensor, for instance associated with the bubble trap 8 or coupled to a portion of the line 7 between the bubble trap 8 and the clamp 9 may be present. If present, the bubble sensor is coupled to the control unit 14 to enable the control unit 14 to cause closure of the clamp 9 in case a critical number of bubbles is detected, e.g., one or more bubbles above a safety threshold.

The withdrawal line 6 and return line 7 may include any one of the arterial and venous lines of known type used in an apparatus for hemodialysis or hemo(dia)filtration. In particular, the withdrawal line 6 and return line 7 may be equipped with and/or connected to various sensors and actuators of known type (for example, pressure sensors, blood presence sensors or patient presence sensors, liquid level sensors, air presence sensors, blood transport pumps, infusion liquid transport pumps, automatic block valves, liquid level regulation devices, etc.) for the control and monitoring of the circuit itself, and to various devices of known type (gas-liquid separation devices, removal-injection access sites, manual clamps, service lines, etc.) for performing various operations on the circuit. One exemplary device illustrated in FIG. 1 is a blood warmer 10.

Further, in one embodiment, a sensor may be arranged in the extracorporeal blood circuit 3 (e.g., located the blood withdrawal line 6) to emit a signal that is indicative of a change of blood volume of the patient. Such a sensor may include, for example, an optical or acoustic sensor. In one embodiment, the blood volume sensor indicates blood volume changes.

In use, the user may enter a predetermined value for the blood flow rate $Q_{BLOOD}$ using the user interface 12, and the control unit controls during the treatment the pump 11 based on the predetermined blood flow rate.

The apparatus 1 may include a weight loss system to actuate the weight loss of the individual during the extracorporeal blood treatment. Such a weight loss system includes a drain line connected to a fluid chamber outlet for removing a discharge liquid from the chamber and sending it to a drainage (bag or discharge). A sensor generates a signal indicating the weight loss of the individual subjected to extracorporeal blood treatment. The sensor may have sensor means of a known type used for detecting or determining the patient's weight loss in an ultrafiltration, hemodialysis or blood(dia)filtration apparatus. For example, in a hemodiafiltration apparatus, the sensor may have a two-flow meter system of (one upstream and one downstream of the filtering unit 2), or a differential flow meter, or a system of scales, or a control system of the filling of predetermined volumes, or an ultrafiltration flow sensor in a fluid-balancing system with variable volume chambers, or still other systems of known type.

The extracorporeal treatment apparatus may further have a system for supplying a fresh treatment fluid in a predetermined composition. The supply system may comprise any of the supply systems of known type used to supply a dialysis and/or replacement fluid in a hemodialysis or hemo(dia)filtration apparatus (for example of the type with in-line preparation of the treatment fluid from water and concentrates of the type sourcing from a batch-type source such as one or more bags of fluid). The supply system may have a supply line connected to an inlet of a fluid chamber, a source the treatment fluid (batch-type or in-line preparation type) and a supply pump. The sensor is in this case connected to the supply line to take into account, when determining the individual's weight loss, the flow of the treatment fluid, in particular dialysis fluid entering the fluid chamber and/or possibly replacement fluid infused into the extracorporeal circuit 3. The source has a device for in-line preparation of a treatment fluid having a predetermined concentration. The preparation device may comprise any of the devices of known type used in a hemodialysis or hemo(dia)filtration machine. In particular the preparation device may prepare the treatment fluid starting from water and concentrates by using of one or more sensors, for example, an electrical conductivity sensor (or another type of sensor for determining the composition of the dialysis solution) in order to determine, in a known way, the composition of the prepared fluid. The structure and functioning of the preparation device is known.

In use, the hemodiafiltration apparatus operates in a known way to affect a predetermined weight loss in the patient, giving rise to an ultrafiltration device for ultrafiltering liquid from the blood chamber 15 to the fluid chamber 16 through the semipermeable membrane 17. In particular, the ultrafiltration is carried out by exploiting the pressure difference at the two sides of the membrane 17 (transmembrane pressure, or TMP) and the resulting convective transport of liquid generated by a discharge pump which enables having a pressure in the chamber fluid that is lower than the pressure in the blood chamber. The ultrafiltration means are of known.

The apparatus may also include an infusion device for infusing liquid into the extracorporeal circuit. The infusion device may include an infusion line and an infusion pump for moving the infusion fluid. The infusion line is connected in a branched relationship with the supply line, from a branch point positioned downstream of the sensor. The infusion line may be connected to a batch source of infusion fluid. In the illustrated example the infusion line is connected to the return line (post-dilution), although in addition to or as an alternative to the line 18 an infusion line may be provided, not shown, connected to the removal line (pre-dilution).

The user interface 12 allows input of data, such as patient information, desired weight loss or desired weight loss rate, treatment time, significant parameters of the treatment and/or of the individual, etc. The user interface also displays and/or visually outputs data, such as patient information, treatment information and/or significant parameters of the treatment and/or of the individual, acoustic and/or visual alarms, etc.

In one embodiment, the control unit 14 is configured to receive signals of relative change of blood volume and (variation of) weight loss during extracorporeal blood treatment, in order to verify whether the relationship between the relative change of blood volume and the change in the weight loss of the individual is in a predetermined relationship with a desired value, and to control the weight loss system on the basis of the above verification.

The control unit 14 is configured to carry out the above receiving operations of verification and control signals iteratively during treatment. Of course the control unit 14 may receive the desired value as an input from an operator. The desired value may be a fixed value or a profile of desired values over the time.

The patient-specific prescription parameter provides useful information for understanding the response of the patient undergoing dialysis, in particular of his or her behavior relating to what is known as vascular "refilling", i.e. the amount of fluid that moves from the interstitial space of the patient's body to the intravascular space. During treatment the mass of accumulated liquids is subtracted from the blood plasma through the ultrafiltration function, which then has the task of reabsorbing from the cells of the tissues. Physiologically, this reconstitution (refilling) occurs quite slowly because it in turn depends on the permeability of the cell membrane and the extra-intracellular gradient, so that immoderate removal may cause significant side effects such as collapse and cramps. The control system of the apparatus is able to ensure accuracy of extractions and treatment comfort by following this parameter and the desired value (or performance) thereof during treatment.

The above parameter of the individual optionally comprises a refilling index IR that may be defined by:

$$IR = \frac{\Delta BV\ \%}{\Delta WL\ \%}$$

or by:

$$IR = \frac{\Delta WL\ \%}{\Delta BV\ \%}$$

where $\Delta BV\ \%$ is the relative variation of blood volume, i.e. the variation in blood volume as a ratio of the total blood volume, and $WL\ \%$ is the relative weight drop, i.e. the weight drop as a ratio of the total weight of the individual or the weight of the individual's body water.

The patient-specific prescription parameter may be any function of the refilling index and in particular it might be proportional to the refilling index IR or coincident with the refilling index IR.

In the description that follows, we will examine the case relating to the second definition of the index IR $$\left(IR = \frac{\Delta WL\ \%}{\Delta BV\ \%}\right),$$

but naturally the same approach may be obtained by exploiting the first definition of the refilling index and therefore the detailed description below is not intended as a factor that limits the invention.

The control unit 14 may also be configured to receive a minimum threshold value and/or a maximum threshold value of acceptability for the aforementioned set value. In a case in which the individual parameter is the refilling index, the above-mentioned minimum threshold value may be comprised, for example, between 0.6 and 1.1, while the above-mentioned maximum threshold value may be comprised, for example, between 1.1 and 1.6.

The above-cited verification may comprise verifying if:

$$\frac{\Delta BV\ \%(t)}{WL(t)} = \frac{IR(t)}{TW} = \frac{IR_{des}(t)}{TW}$$

where $\Delta BV\ \%(t)$ is the relative variation of blood volume at time t, $WL(t)$ is the weight loss at time t, $IR(t)$ is the calculated value of the refilling index at time t, $IR_{des}(t)$ is the desired value of the refilling index at time t, TW is a weight value of the individual. Even TW may be a value $TW(t)$ dependent on the treatment time, for example if we consider the value $TW(t)$ of the patient's weight (total weight or weight of body water) at time t, i.e. taking into account the weight loss $WL(t)$ reached precisely at time t. In this case the weight at time t will be $TW(t)=TW_0-WL(t)$, where $TW_0$ is the patient's weight (total weight or weight of body water) at the beginning of treatment.

The above-mentioned weight value of the individual may optionally comprise a value selected from between the total body weight of the individual before or after the treatment, the weight of the body water of the individual before or after the treatment, the total body weight or the weight of the body water of the individual at a specific time during the extracorporeal treatment of blood.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. An extracorporeal blood treatment system comprising: a first holder, the first holder holding when the system is in use a blood treatment device having a blood chamber, a fluid chamber, and a semipermeable membrane that separates the chambers from each other; a second holder, the second holder holding when the system is in use an extracorporeal blood circuit coupled to the blood treatment device; and a control unit configured to operate at least one pump to cause blood to flow through the blood treatment device and the extracorporeal blood circuit, wherein the control unit is further configured to execute a procedure comprising:

prior to commencing an extracorporeal blood treatment, reading from a storage device stored values of a water-refilling index, wherein the stored values relate to a sequence of previous extracorporeal blood treatments, processing the stored values of the water-refilling index read from the storage device according to an algorithm to determine a current value of the water-refilling index, wherein the current value is then available for a subsequent extracorporeal blood treatment, and using a default value as the current value if less than a threshold number of stored values is read, deeming valid the current value if within a predetermined range of acceptability, and if not, discarding the current value, wherein the predetermined range of acceptability for the water refilling index is between 0.5 and 2.0.

2. The system of claim 1, wherein the procedure further comprises storing a value of the water-refilling index in the storage device at an end of the extracorporeal blood treatment.

3. The system of claim 2, wherein the procedure further comprises determining that a run-in period is complete when a number of values of the water-refilling index has been stored.

4. The system of claim 3, wherein during the run-in period a treatment is performed without use of historic patient data.

5. The system of claim 1, wherein reading includes reading the stored values according to a pattern.

6. The system of claim 1, wherein the algorithm determines an average value of the stored values read from the storage device.

7. The system of claim 1, wherein the water refilling index is defined by the relation between a total body water volume and a blood volume of a patient to receive the extracorporeal blood treatment.

8. The system of claim 1, wherein the storage device includes a chip card, magnetic card, RFID card, USB memory device or disc storage device.

9. The system of claim 1, which further includes at least one of a network interface for communications with a computer system having a storage device or a communications interface for communications with a storage device.

10. The system of claim 1, wherein the water-refilling index is determined at the end of the extracorporeal blood treatment.

11. The system of claim 1, wherein the procedure is executed before performing the extracorporeal blood treatment with values of the water-refilling index from the last N extracorporeal blood treatments, in order to implement an "observation window" moving over time.

12. The system of claim 1, wherein the procedure is continuously executed to track a change of a patient's physical characteristics over time.

13. A method of operating an extracorporeal blood treatment system including a first holder for a blood treatment device having a blood chamber, a fluid chamber and a semipermeable membrane that separates the chambers from each other, a second holder for an extracorporeal blood circuit connectable to the blood treatment device, and a control unit configured to operate at least one pump to cause blood to flow through the blood treatment device and the extracorporeal blood circuit, the method comprising:

prior to commencing an extracorporeal blood treatment, reading from a storage device stored values of a patient-specific prescription parameter, the patient-specific prescription parameter including an end-of-treatment parameter from the group including: a water-refilling index, a final relative blood volume, a final blood volume, or a variation of weight loss, wherein the stored values relate to a sequence of previous extracorporeal blood treatments;

processing the stored values of the prescription parameter read from the storage device according to an algorithm to determine a current value of the patient-specific prescription parameter, wherein the current value is then available for a subsequent extracorporeal blood treatment; and using a default value as the current value if less than a threshold number of stored values is read, deeming valid the current value if within a predetermined range of acceptability, and if not, discarding the current value, and if the current value is deemed valid, (i) prompting a user to accept or discard the suggested value, or (ii) using the current value for the patient-specific prescription parameter.

14. The method of claim 13, which further comprises storing a value of the patient-specific prescription parameter in the storage device at an end of the extracorporeal blood treatment, automatically or under specific action requested by a user.

15. The method of claim 14, which further comprises determining that a run-in period is complete when a number of values of the prescription parameter has been stored.

16. The method of claim 15, wherein during the run-in period a extracorporeal blood treatment is performed without use of historic patient data.

17. The method of claim 13, wherein reading includes reading the stored values according to a pattern.

18. The method of claim 13, wherein the algorithm determines an average value of the stored values read from the storage device.

19. The method of claim 13, further comprising using a user settable default value.

20. The method of claim 13, which is applied before each extracorporeal blood treatment with values of the prescription parameter from the last N treatments, in order to implement an observation window moving over time.

21. The method of claim 13, which is continuously applied to track a change of a patient's physical characteristics over time.

22. The method of claim 13, wherein the patient-specific prescription parameter is a water-refilling index or a function of the water-refilling index.

23. The method of claim 13, wherein the system includes a communications interface for communication with the storage device.

24. The method of claim 20, wherein the mean value of the patient-specific prescription parameter is calculated from the available values from the last N treatments, and wherein an alarm is generated if the current value of the patient-specific prescription parameter deviates from the mean value by a set threshold.

25. The method of claim 20, wherein the mean value of the patient-specific prescription parameter is calculated from the available values from the last N treatments, and wherein the mean value is suggested to the user as the set value if the current value of the patient-specific prescription parameter deviates from the mean value by a set threshold.

26. The method of claim 13, which is performed for multiple patient specific parameters selected from the group consisting of: a water-refilling index, a final relative blood volume, a final blood volume, or a variation of weight loss.

27. The method of claim 13, which includes using a network interface for reading the storage device remotely.

28. The method of claim 13, wherein the system includes a blood treatment machine providing the first and second holders and performing the extracorporeal blood treatment, the blood treatment machine configured to read the storage device.

29. The method of claim 13, wherein the water refilling index is defined by the relation between a total body water volume and a blood volume of a patient to receive the extracorporeal blood treatment.

30. An extracorporeal blood treatment system comprising:
a first holder, the first holder holding when the system is in use a blood treatment device having a blood chamber, a fluid chamber and a semipermeable membrane that separates the chambers from each other;
a second holder, the second holder holding when the system is in use an extracorporeal blood circuit coupled to the blood treatment device; and
a control unit configured to operate at least one pump to cause blood to flow through the blood treatment device and the extracorporeal blood circuit, wherein the control unit is further configured to execute a procedure comprising:

prior to commencing an extracorporeal blood treatment, reading from a storage device stored values of a patient-specific prescription parameter, the patient-specific prescription parameter being an end-of-treatment parameter from the group including a water-refilling index, a final relative blood volume, a final blood volume, or a variation of weight loss, wherein the stored values relate to a sequence of previous extracorporeal blood treatments, processing the stored values of the prescription parameter read from the storage device according to an algorithm to determine a current value of the patient-specific prescription parameter, wherein the current value is then available for a subsequent extracorporeal blood treatment, using a default value as the current value if less than a threshold number of stored values is read, deeming valid the current value if within a predetermined range of acceptability, and if not, discarding the current value, and once the current value is deemed valid, (i) suggesting the current value to the user and requiring him/her to either accept or discard the suggested value, or (ii) using the current value as a set value for the patient-specific prescription parameter.

31. The system of claim 30, wherein the patient-specific prescription parameter is a water-refilling index or a function of the water-refilling index.

32. The system of claim 1, wherein the water-refilling index is defined by:

$$IR = \frac{\Delta BV\ \%}{\Delta WL\ \%} \text{ or } IR = \frac{\Delta WL\ \%}{\Delta BV\ \%},$$

where $\Delta BV\ \%$ is a relative variation of blood volume, and $\Delta WL\ \%$ is a relative weight drop.

33. The method of claim 13, wherein the water-refilling index is defined by:

$$IR = \frac{\Delta BV\ \%}{\Delta WL\ \%} \text{ or } IR = \frac{\Delta WL\ \%}{\Delta BV\ \%},$$

where $\Delta BV\ \%$ is a relative variation of blood volume, and $\Delta WL\ \%$ is a relative weight drop.

34. The system of claim 30, wherein the water-refilling index is defined by:

$$IR = \frac{\Delta BV\ \%}{\Delta WL\ \%} \text{ or } IR = \frac{\Delta WL\ \%}{\Delta BV\ \%},$$

where $\Delta BV\ \%$ is a relative variation of blood volume, and $\Delta WL\ \%$ is a relative weight drop.

\* \* \* \* \*